(12) United States Patent (10) Patent No.: US 8,714,016 B2
Stewart et al. (45) Date of Patent: May 6, 2014

(54) TENSION WAVE GENERATION SYSTEM

(75) Inventors: Alan Frank Stewart, Renton, WA (US);
Richard H. Bossi, Renton, WA (US);
Clarence L. Gordon, III, Renton, WA (US)

(73) Assignee: The Boeing Company, Chicago, IL (US)

( * ) Notice: Subject to any disclaimer, the term of this patent is extended or adjusted under 35 U.S.C. 154(b) by 262 days.

(21) Appl. No.: 13/363,885

(22) Filed: Feb. 1, 2012

(65) Prior Publication Data

US 2013/0192373 A1 Aug. 1, 2013

(51) Int. Cl.
*G01N 29/04* (2006.01)
*G01N 3/00* (2006.01)

(52) U.S. Cl.
USPC .................................. 73/588; 73/827; 73/796

(58) Field of Classification Search
USPC ........... 73/588, 582, 579, 611–612, 614–617, 73/596–601, 587, 589, 796, 818–819, 73/826–827, 801, 842
See application file for complete search history.

(56) References Cited

U.S. PATENT DOCUMENTS

| | | | | |
|---|---|---|---|---|
| 4,184,373 A | * | 1/1980 | Evans et al. | 73/588 |
| 4,484,820 A | * | 11/1984 | Rosencwaig | 374/6 |
| 4,538,462 A | * | 9/1985 | Hartog et al. | 73/577 |
| 5,431,324 A | * | 7/1995 | Kajiwara et al. | 228/102 |
| 6,302,314 B1 | * | 10/2001 | Horio et al. | 228/103 |
| 6,490,047 B2 | * | 12/2002 | Siu | 356/502 |
| 6,491,685 B2 | | 12/2002 | Visuri et al. | |
| 6,622,568 B2 | * | 9/2003 | Nelson et al. | 73/800 |
| 6,848,321 B2 | | 2/2005 | Bossi et al. | |
| 7,017,422 B2 | * | 3/2006 | Heyman et al. | 73/827 |
| 7,341,758 B2 | * | 3/2008 | Stewart et al. | 427/8 |
| 7,487,684 B2 | * | 2/2009 | Gupta et al. | 73/800 |
| 7,507,312 B2 | | 3/2009 | Bossi et al. | |
| 7,509,876 B1 | | 3/2009 | Sokol et al. | |
| 7,770,454 B2 | | 8/2010 | Sokol et al. | |
| 7,900,516 B2 | * | 3/2011 | Fukutomi et al. | 73/598 |
| 8,132,460 B1 | * | 3/2012 | Toller et al. | 73/588 |
| 8,359,924 B1 | * | 1/2013 | Bossi et al. | 73/588 |

* cited by examiner

*Primary Examiner* — Helen Kwok
(74) *Attorney, Agent, or Firm* — Yee & Associates, P.C.

(57) ABSTRACT

A method and apparatus for generating a tension wave. A beam of coherent light is directed to an absorber surface of a transducer structure. A compression wave is generated within the transducer structure. The compression wave is reflected on a reflecting surface of the transducer structure to form the tension wave. The tension wave is directed through a test object in a desired direction using a configuration of the reflecting surface relative to the test object.

20 Claims, 11 Drawing Sheets

TENSION WAVE GENERATION SYSTEM

BACKGROUND INFORMATION

1. Field

The present disclosure relates generally to testing objects and, in particular, to testing the strength of bonds in objects. Still more particularly, the present disclosure relates to a method and apparatus for testing the strength of bonds in a bonded structure using tension waves.

2. Background

A composite object may be comprised of one or more composite structures that are bonded to each other. Identifying and certifying the strength of bonds may be performed for different applications that use composite structures. These applications include their use in platforms, such as aircraft.

One manner in which bonds may be tested is through the use of laser bond inspection. Laser bond inspection tests the strength of bonds between composite structures within a composite object. In this technique, weak bonds may be "pulled apart" by tension waves traveling through the structure.

With laser bond inspection, a laser beam is directed at the front surface of a composite object. The laser beam creates mechanical waves in the form of compression waves that travel through the composite object toward the back surface of the composite object. When the compression wave reaches a back surface of the object under test, the compression wave is reflected back from that surface producing a tension wave that propagates back toward the front surface of the object. The tension waves apply tension to the internal structure of the object, including any bond lines between the front and back surface of the object. The tension waves may have a sufficient strength that is selected to determine whether bonds between the parts of the object have a desired strength.

Laser bond inspection may be considered a non-destructive testing method when the bonds between composite structures are sufficiently strong. If a tension wave encounters a bond within the composite object that has the desired strength, the bond remains intact and inconsistencies are absent. The composite object may be examined to determine whether any inconsistencies are present in the composite object. If the bond is sufficiently strong, the composite object is not altered and may be used in different applications. This composite object also may be certified as providing a selected strength value.

If the tension wave encounters a bond within the composite object that does not have the desired strength, an inconsistency may occur. If an inconsistency is present, the composite object does not have the desired strength and may be discarded, reworked, or otherwise processed.

Laser bond inspection may require more equipment or cost than desired. Further, the dimensions of the composite object may limit the usefulness of laser bond inspection. For example, both the compression and tension waves lose strength while traveling through the composite object. When testing larger or denser composite objects, the resulting tension wave may not generate as much force as desired. In other words, as the distance increases from the surface of the composite structure to the back surface of the structure, the strength of the tension wave also decreases. The type of material also may reduce the strength of the tension wave as it travels through the composite object.

As a result, a larger compression wave is needed to produce a tension wave with the desired strength to accurately test the bonds between parts of an object. A larger compression wave requires more energy from the laser, which requires a larger and more expensive laser unit.

Using laser bond inspection also may be difficult for irregularly-shaped objects. For irregularly-shaped objects, the waves may reflect irregularly, further decreasing the strength of the reflected tension wave. Irregularly-shaped objects may also fail to properly direct tension waves to locations of interest within the structure. As a result, testing bonds in a composite object with compression waves produced by a laser may have limited application and may not produce the desired results.

Therefore, it would be desirable to have a method and apparatus that takes into account one or more of the issues discussed above, as well as possibly other issues.

SUMMARY

In one illustrative embodiment, a method for generating a tension wave is present. A beam of coherent light is directed to an absorber surface of a transducer structure. A compression wave is generated within the transducer structure. The compression wave is reflected on a reflecting surface of the transducer structure to form the tension wave. The tension wave is directed through a test object in a desired direction using a configuration of the reflecting surface relative to the test object.

In another illustrative embodiment, a method for generating a tension wave is present. A laser beam is directed to an absorber connected to an absorber surface of a transducer structure. The absorber is configured to absorb energy in the laser beam and generate a compression wave within the transducer structure. The compression wave is reflected on a reflecting surface of the transducer structure to form the tension wave. The tension wave is directed through a test object in a desired direction. The reflecting surface has a configuration relative to the test object that causes the tension wave to move in the desired direction.

In yet another illustrative embodiment, an apparatus comprises a transducer structure, an absorber surface on the transducer structure, a reflecting surface on the transducer structure, and a coupling surface on the transducer structure. The absorber surface is configured to receive energy configured to cause a compression wave. The reflecting surface is configured to reflect the compression wave traveling from the absorber surface to generate a tension wave in a desired direction using a configuration of the reflecting surface. The compression wave is generated by an absorber coupled to the absorber surface and absorbs the energy from a beam of coherent light. The coupling surface is configured to be coupled to a test object. The tension wave travels through the test object in the desired direction.

The features, functions, and advantages can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives, and advantages thereof will best be understood by reference to the following detailed description of an illustrative embodiment of the present disclosure when read in conjunction with the accompanying drawings, wherein:

DETAILED DESCRIPTION

Figure 1:
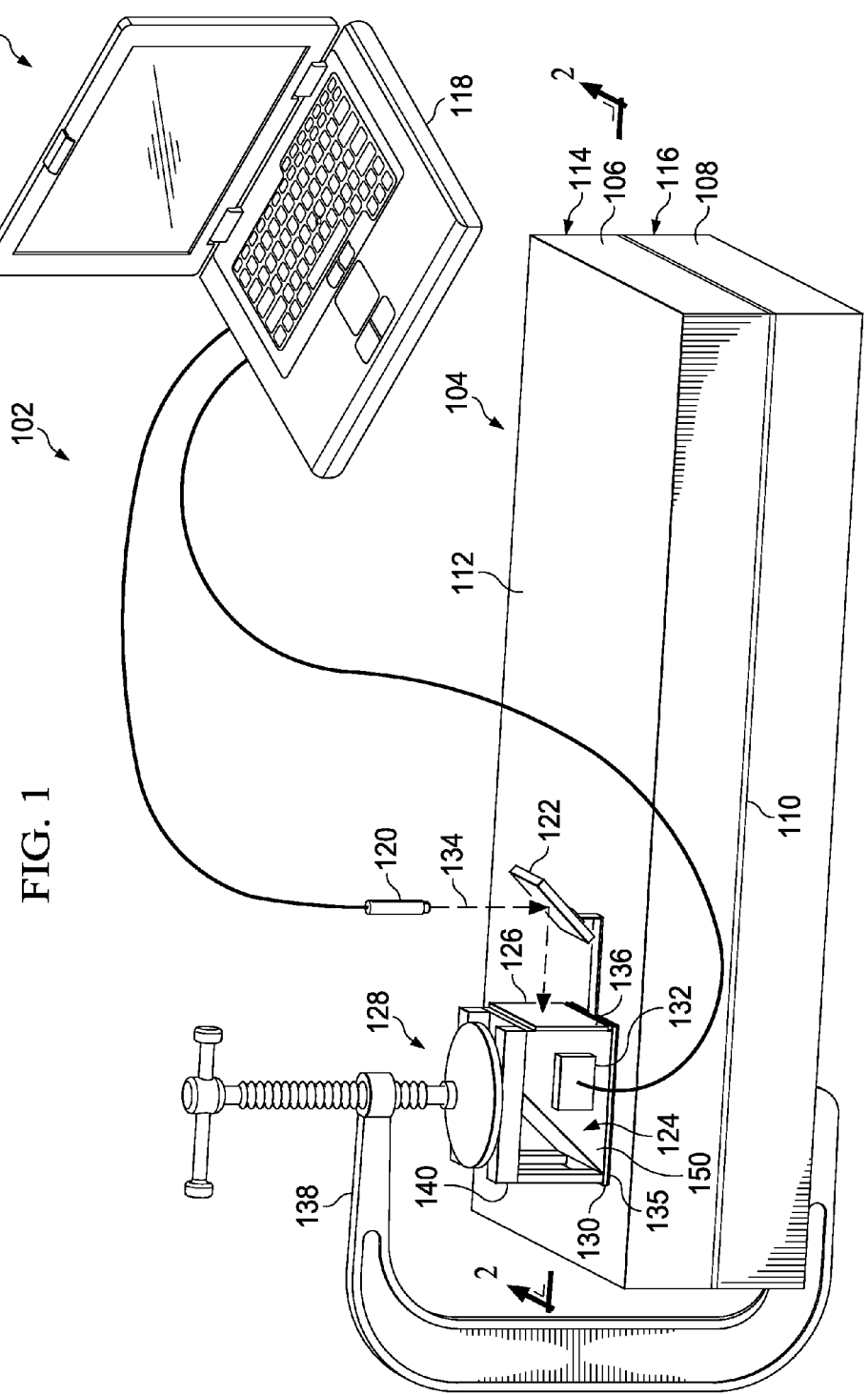
FIG. 1 is an illustration of a test environment for testing bonds in a test object in accordance with an illustrative embodiment.

With reference now to the figures and, in particular, with reference to FIG. 1, an illustration of a test environment for testing bonds in a test object is depicted in accordance with an illustrative embodiment. In this illustrative example, test environment 100 includes inspection system 102 and test object 104.

As depicted, inspection system 102 is used to perform an inspection of test object 104. More specifically, inspection system 102 may be used to perform an inspection of a number of bonds in test object 104.

As depicted in this illustrative example, test object 104 comprises first structure 106 and second structure 108 that are bonded to each other. In these illustrative examples, first structure 106 and second structure 108 may be bonded to each other in a number of different ways. For example, first structure 106 and second structure 108 may be bonded to each other using an adhesive. The adhesive may be formed from a number of materials that may be organic, inorganic, or a combination of the two.

The interface where first structure 106 and second structure 108 are bonded to each other is bond line 110. Bond line 110 may be planar or non-planar, depending on the particular implementation. In these illustrative examples, test object 104 may be comprised of any type of material. As depicted, test object 104 is composite object 112. Further, first structure 106 is first composite structure 114 and second structure 108 is second composite structure 116.

In these illustrative examples, inspection system 102 may test the strength of a number of bonds in test object 104. As used herein, a "number", used with reference to items, means one or more items. For example, a "number of bonds" is one or more bonds. As depicted, inspection system 102 includes computer 118, laser unit 120, reflecting system 122, transducer structure 124, absorber 126, coupling system 128, acoustic matching layer 130, and transducer system 132.

Laser unit 120 and transducer system 132 are connected to computer 118. In these illustrative examples, the connection is an electrical connection that allows computer 118 to control the operation of laser unit 120 and transducer system 132.

In this illustrative example, laser unit 120 is configured to generate beam of coherent light 134 and send beam of coherent light 134 toward reflecting system 122 in the direction shown for beam of coherent light 134. As depicted, beam of coherent light 134 takes the form of a laser beam. In these illustrative examples, the laser beam may be generated as a pulse. The pulse may have different lengths. For example, the pulse may be about 300 nanoseconds or less in duration.

Reflecting system 122 is configured to direct beam of coherent light 134 generated by laser unit 120 toward absorber surface 136 on transducer structure 124. Reflecting system 122 takes the form of a mirror in this illustrative example. In other illustrative examples, additional mirrors or other components may be part of reflecting system 122.

As depicted, absorber 126 is connected to absorber surface 136. Absorber 126 is configured to absorb the coherent light in beam of coherent light 134 and generate a compression wave inside of transducer structure 124. In these illustrative examples, when absorber 126 absorbs coherent light in beam of coherent light 134, absorber 126 heats and forms a plasma. The plasma causes a compression wave to be generated.

Transducer structure 124 is configured to create a tension wave from the compression wave and direct the tension wave through test object 104. In these illustrative examples, a tension wave is a wave that causes stress within a structure in which the tension wave propagates. The tension wave pulls on a structure instead of compressing a structure. The tension wave may pull on a structure or may pull two structures bonded to each other in a direction away from each other.

In this illustrative example, transducer structure 124 has prism shape 150. In other words, transducer structure 124 may take the form of a prism in some illustrative examples. Transducer structure 124 may be comprised of one or more materials that provide a desired level of strength of sound waves, a desired propagation of sound waves, or a combination of the two. In other words, the number of materials selected for transducer structure 124 may be selected such that the materials provide a low enough loss when sound waves propagate through those materials. Material selected for transducer structure 124 also may be selected to have a desired level of density and weight.

Acoustic matching layer 130 is located between transducer structure 124 and test object 104. Acoustic matching layer 130 also couples transducer system 132 to test object 104. In these illustrative examples, acoustic matching layer 130 is configured to increase a transfer of energy in the tension wave sent from transducer structure 124 through test object 104. As depicted, acoustic matching layer 130 also serves to increase the efficiency of coupling between transducer system 132 and test object 104.

Coupling system 128 is configured to apply force or pressure to transducer structure 124 toward test object 104. As depicted, coupling system 128 comprises clamp 138 and clamping structure 140. Clamp 138 couples transducer structure 124 to test object 104. Clamping structure 140 is configured to aid in connecting clamp 138 to transducer structure 124.

Coupling system 128 also may include bonding agent 135. As depicted, bonding agent 135 may be used to temporarily bond transducer structure 124 to test object 104. The bond may be generated using a material, such as an adhesive or other suitable bonding agent. The adhesive may be applied to acoustic matching layer 130. If acoustic matching layer 130 is not used, the adhesive may be directly applied to transducer structure 124.

In these illustrative examples, transducer system 132 may be coupled to transducer structure 124 and configured to determine whether an inconsistency in the number of bonds is present in test object 104. This determination may be made after the tension wave travels through test object 104. In these illustrative examples, transducer system 132 is a piezoelectric transducer system. One or more additional tension waves may be generated by transducer structure 124. Transducer system 132 may generate signals. A response signal to the tension waves, the signals, or a combination of the two may be detected by transducer system 132.

The illustration of test environment 100 is not meant to imply physical or architectural limitations to the manner in which test environment 100 may be implemented. For example, inspection system 102 may include other types of coupling systems other than clamp 138 in these illustrative examples. For example, in other illustrative examples, transducer structure 124 may be bonded to test object 104. In still other illustrative examples, a weight may be placed on transducer structure 124. Further, transducer system 132 also may be placed on test object 104 rather than on transducer structure 124. In still other illustrative examples, transducer system 132 may be omitted or some other type of inspection system may be used.

As yet another illustrative example, absorber 126, acoustic matching layer 130, or both may be omitted in some illustrative examples. Further, transducer structure 124 may be used to test the strength of first structure 106, second structure 108, or both in addition to or in place of testing the bond between these two structures in test object 104. Although test object 104 is shown as composite object 112, test object 104 may be another type of object other than composite object 112. For example, test object 104 may be comprised of metal, plastic, wood, and/or other types of structures in addition to or in place of composite materials.

Figure 2:
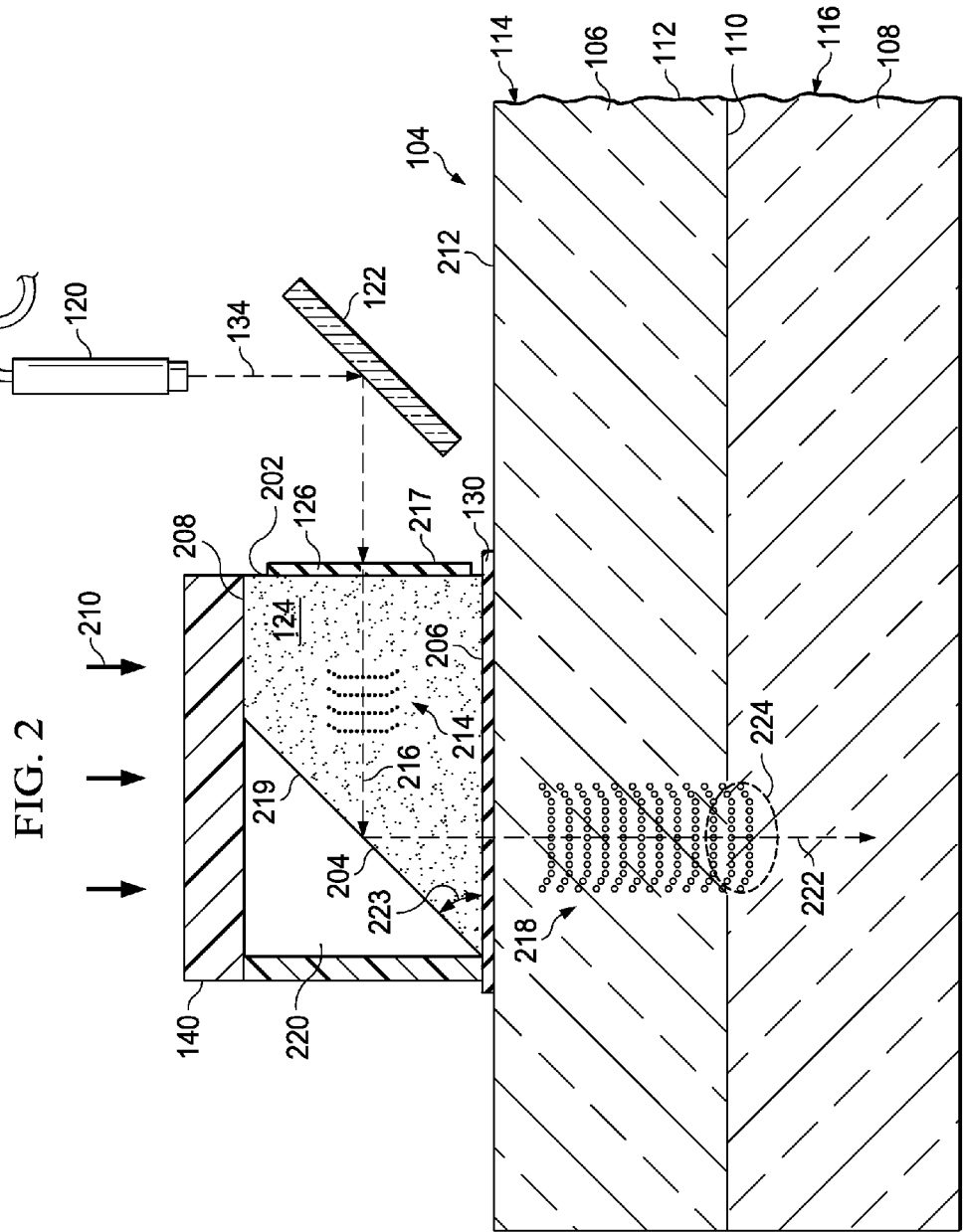
FIG. 2 is an illustration of a cross-sectional view of a portion of a test environment in accordance with an illustrative embodiment.

Turning now to FIG. 2, an illustration of a cross-sectional view of a portion of a test environment is depicted in accordance with an illustrative embodiment. In this illustrative example, a cross-sectional view of some components of test environment 100 is seen taken along lines 2-2.

In this cross-sectional view, transducer structure 124 has absorber surface 202, reflecting surface 204, coupling surface 206, and clamping surface 208. Clamping surface 208 is configured to be in contact with clamping structure 140 such that force 210 may be applied to clamping structure 140 to couple transducer structure 124 to surface 212 of test object 104.

In these illustrative examples, transducer structure 124 may be comprised of a number of different materials. Transducer structure 124 may be comprised of a material selected from at least one of a metal, a metal alloy, titanium, aluminum, steel, and other suitable materials.

As used herein, the phrase "at least one of", when used with a list of items, means different combinations of one or more of the listed items may be used and only one of each item in the list may be needed. For example, "at least one of item A, item B, and item C" may include, without limitation, item A or item A and item B. This example also may include item A, item B, and item C, or item B and item C.

As depicted, absorber 126 is connected to absorber surface 202. Absorber 126 may be comprised of a number of different materials. For example, absorber 126 may be a liquid, a solid, or some other suitable material. The number of materials for absorber 126 may be selected from materials that absorb energy from beam of coherent light 134.

For example, the number of materials for absorber 126 may be selected from at least one of carbon black, black chrome plating, pyrolytic carbon, flat black paint, vinyl tape, and other materials with a desired level of optical absorption. These materials may also be selected as ones that may be replenished as easily as desired.

These materials also may be selected as ones that may be bonded using adhesive or otherwise mechanically fixed to absorber surface 202 between tests. Absorber 126 may take a number of different forms. For example, without limitation, absorber 126 may be in the form of tape, paint, adhesive, a liquid, a paste, or some other suitable form that can be placed on absorber surface 202.

In these illustrative examples, acoustic matching layer 130 is located between transducer structure 124 and test object 104. In particular, acoustic matching layer 130 is coupled to coupling surface 206 on transducer structure 124 and surface 212 of test object 104. Acoustic matching layer 130 may be comprised of a number of different materials.

Acoustic matching layer 130 may be implemented using any material that increases the amount of energy transferred by waves traveling from transducer structure 124 into test object 104. For example, acoustic matching layer 130 may be comprised of one or more materials including metals, such as aluminum, magnesium, tin, and alloys of these and other suitable materials. As another illustrative example, the one or more materials may include a metal-filled epoxy compound, an epoxy compound with a filler, and/or other materials that provide a desired acoustic impedance. The materials selected for acoustic matching layer 130 may be selected as any material having desired impedance properties, physical thickness, and/or durability.

In these illustrative examples, energy may be applied to transducer structure 124. In particular, the energy takes the form of beam of coherent light 134 emitted by laser unit 120. Beam of coherent light 134 is directed toward absorber surface 202 on transducer structure 124. Absorber 126 is configured to absorb the coherent light in beam of coherent light 134 in a manner that generates compression wave 214 that travels in direction 216.

Additionally, tamping layer 217 also may be present. Tamping layer 217 is configured to direct energy generated by beam of coherent light 134 being absorbed by absorber 126 inwards in direction 216. In these illustrative examples, when absorber 126 absorbs the coherent light in beam of coherent light 134, a plasma may be generated. This plasma causes compression wave 214 in transducer structure 124 in these illustrative examples.

When compression wave 214 reaches reflecting surface 204, compression wave 214 is reflected by reflecting surface 204 to generate tension wave 218. In these illustrative examples, tension wave 218 is generated as a result of interface 219 between dissimilar media. In particular, interface 219 at reflecting surface 204 is an interface between the material comprising transducer structure 124 and air 220. In these illustrative examples, reflecting surface 204 may be a hypotenuse for transducer structure 124.

As depicted, the material in transducer structure 124 has a higher acoustic impedance as compared to air 220 in these illustrative examples. This difference in acoustic impedance causes compression wave 214 to be converted into tension wave 218 in these depicted examples. Of course, another medium other than air 220 may be used. If another medium is selected, that medium is selected to have a lower acoustic impedance as compared to the material in transducer structure 124.

Tension wave 218 travels through test object 104 in desired direction 222. In these illustrative examples, desired direction 222 is a desired direction for tension wave 218 to test the bond between first structure 106 and second structure 108 in test object 104. Desired direction 222 may be generated based on the configuration of reflecting surface 204. In this illustrative example, reflecting surface 204 has angle 223 relative to reflecting surface 204. Further, the shape, focus, and other characteristics of tension wave 218 may be controlled based on the configuration of reflecting surface 204.

In these illustrative examples, the configuration of reflecting surface 204 relative to test object 104 may include at least one of an orientation of reflecting surface 204, a shape of reflecting surface 204, and other parameters for reflecting surface 204. In this illustrative example, reflecting surface 204 is planar. The planar shape of reflecting surface 204 results in tension wave 218 being substantially planar.

In other examples, reflecting surface 204 may have other shapes. For example, reflecting surface 204 may be concave, convex, non-uniform, or have some other suitable shape.

In these illustrative examples, tension wave 218 travels through transducer structure 124 and then through acoustic matching layer 130 into test object 104. Tension wave 218 travels to bond line 110 to generate stress at bond line 110.

In these illustrative examples, tension wave 218 is configured to cause stress zone 224 in test object 104 at bond line 110. The size and shape of stress zone 224 may depend on the size and shape of tension wave 218.

As depicted, tension wave 218 has a strength that tests the bond between first structure 106 and second structure 108. The strength of tension wave 218 may be selected based on a desired strength for the bond between first structure 106 and second structure 108. In other words, the strength of tension wave 218 may be selected to be equal to the desired strength for the bond.

If a desired level of strength is not present in the bond between first structure 106 and second structure 108, an inconsistency may be present in bond line 110 after tension wave 218 passes through bond line 110. The detection of the inconsistency may be performed using transducer system 132 in FIG. 1.

Figure 3:
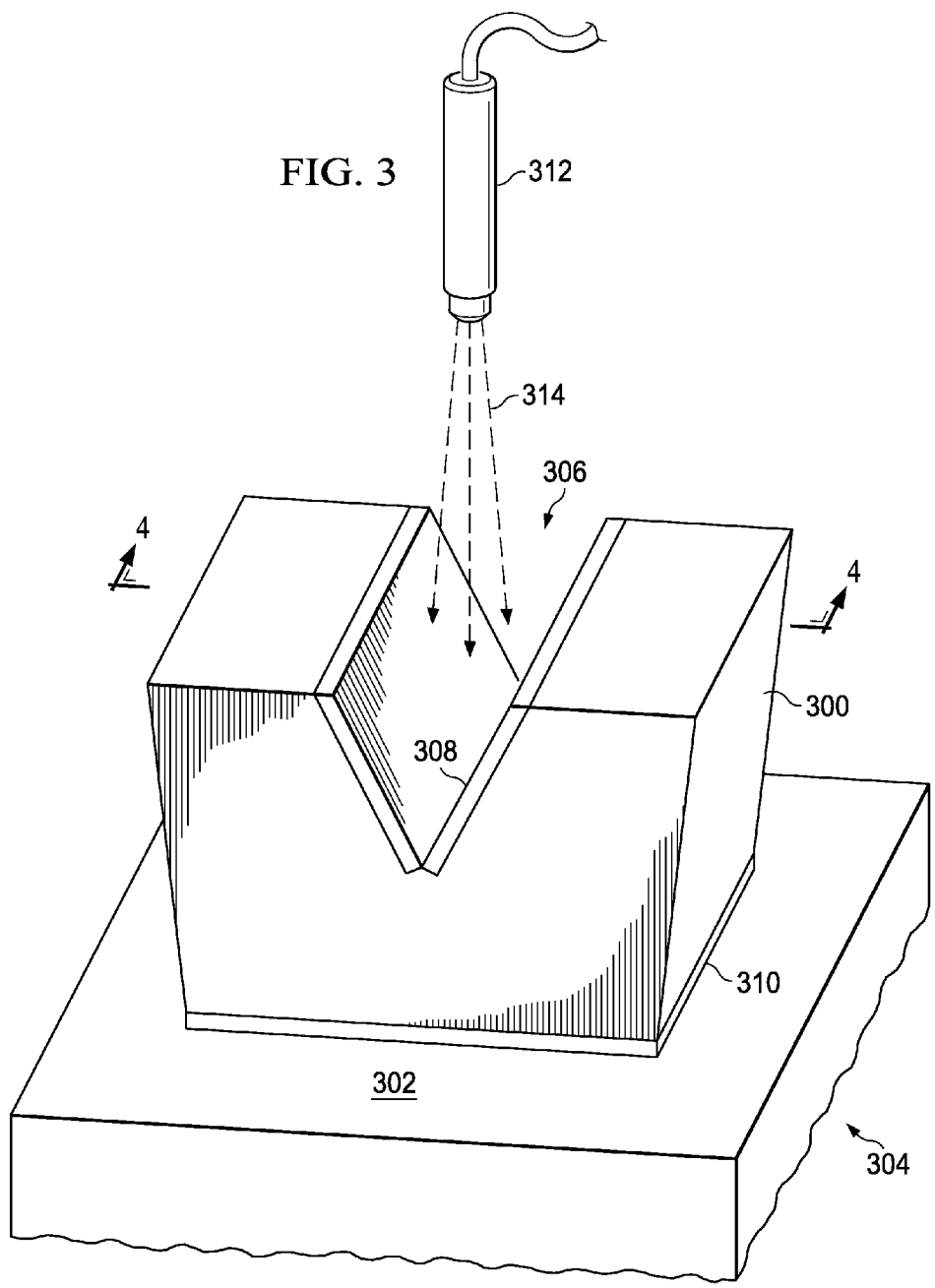
FIG. 3 is an illustration of another configuration for a transducer structure in accordance with an illustrative embodiment.

With reference now to FIG. 3, an illustration of another configuration for a transducer structure is depicted in accordance with an illustrative embodiment. In this illustrative example, transducer structure 300 is shown coupled to surface 302 of test object 304.

In this illustrative example, transducer structure 300 has channel 306 with absorber 308 in channel 306. In this illustrative example, channel 306 has a cross section with a v-shape. As depicted, acoustic matching layer 310 is located between transducer structure 300 and test object 304.

Laser unit 312 applies energy to absorber 308 through beam of coherent light 314. Beam of coherent light 314 is a laser beam in these illustrative examples. In this illustrative example, a reflecting system, such as reflecting system 122 in FIG. 1, is unnecessary in this depicted example.

Figure 4:
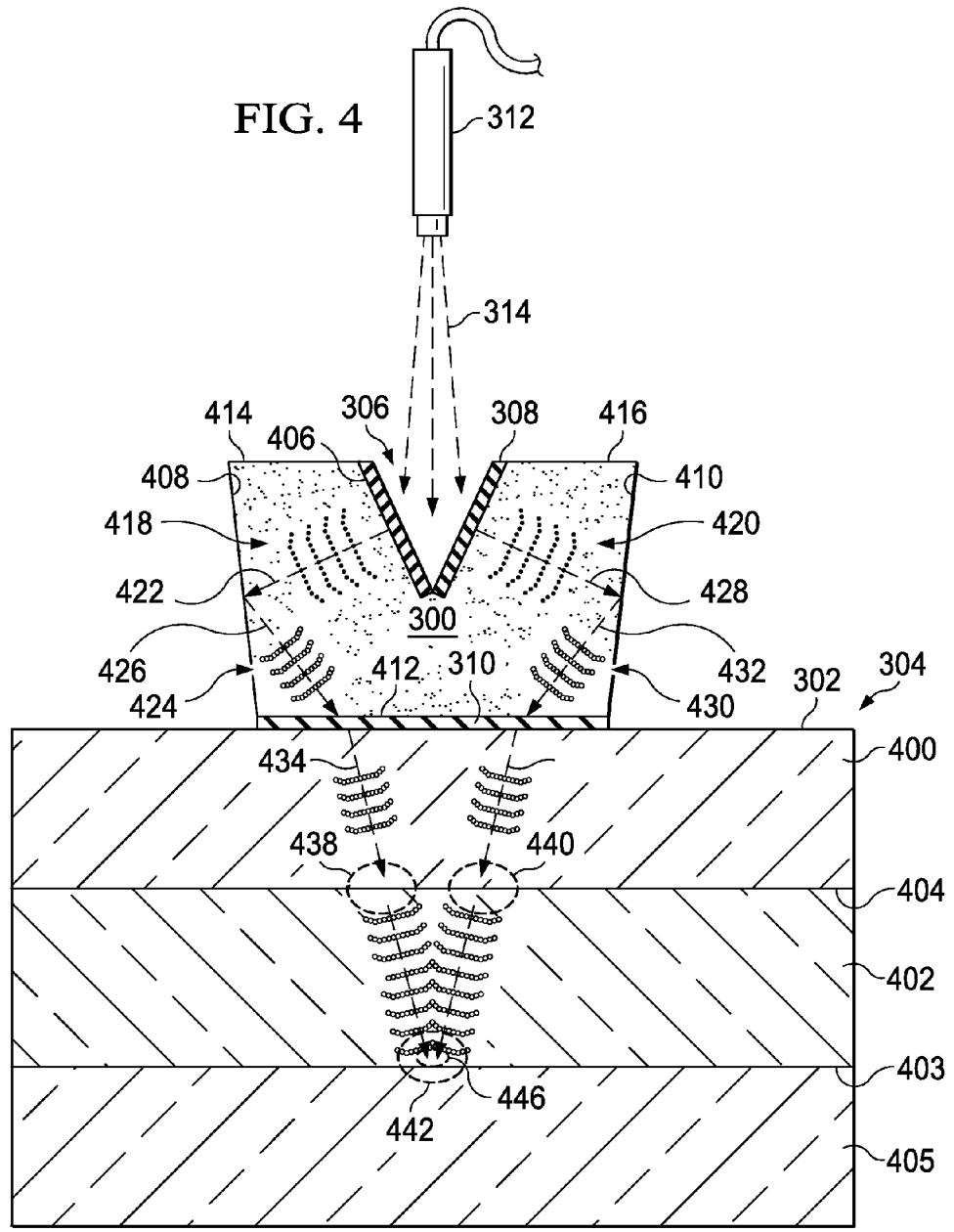
FIG. 4 is a cross-sectional view of a transducer structure on an object in accordance with an illustrative embodiment.

With reference now to FIG. 4, a cross-sectional view of a transducer structure on an object is depicted in accordance with an illustrative embodiment. A cross-sectional view of transducer structure 300 and test object 304 is seen taken along lines 4-4 in FIG. 3.

As depicted, test object 304 is comprised of first structure 400, second structure 402, and third structure 405. These structures are bonded to each other. The interface at which first structure 400 is bonded to second structure 402 is bond line 404. The interface at which second structure 402 is bonded to third structure 405 is bond line 403.

In this configuration, transducer structure 300 has absorber surface 406, reflecting surface 408, reflecting surface 410, coupling surface 412, clamping surface 414, and clamping surface 416. In these illustrative examples, absorber surface 406 is located in channel 306. In other words, absorber surface 406 is the surface that forms the walls of channel 306 in this depicted example.

Absorber 308 is connected to absorber surface 406. Acoustic matching layer 310 is coupled to coupling surface 412 of transducer structure 300 and surface 302 of test object 304. Acoustic matching layer 310 may be bonded to coupling surface 412 and surface 302 through a bonding agent, such as an adhesive, a gel, or some other suitable material.

In this illustrative example, beam of coherent light 314 is directed toward absorber surface 406 of transducer structure 300. Absorber 308 absorbs at least a portion of coherent light in beam of coherent light 314. This absorption of energy results in the generation of compression waves, such as compression wave 418 and compression wave 420. Compression wave 418 travels in direction 422 toward reflecting surface 408. Compression wave 418 reflects off of reflecting surface 408 as tension wave 424 in direction 426.

In a similar fashion, compression wave 420 travels in direction 428 to reflecting surface 410. Compression wave 420 reflects off of reflecting surface 410 as tension wave 430 in direction 432. Tension wave 424 and tension wave 430 travels in direction 426 and direction 432, respectively, through acoustic matching layer 310 and through test object 304 in desired direction 434 and desired direction 436 inside of test object 304.

In this illustrative example, tension wave 424 and tension wave 430, as well as other tension waves that may be generated, cause stress zones within test object 304. These stress zones may include, for example, stress zone 438, stress zone 440, and stress zone 442 in test object 304.

In this illustrative example, stress zone 438 and stress zone 440 encompasses bond line 404. The strength of the tension waves may be used to test whether the bond between first structure 400 and second structure 402 in test object 304 has a desired level of strength. Stress zone 442 encompasses bond line 403 between second structure 402 and third structure 405.

In a similar fashion, the strength of tension wave 424 and tension wave 430 may cause stress within test object 304 to determine whether the bond between second structure 402 and third structure 405 has a desired level of strength. In other words, the strength of tension wave 424 and tension wave 430 may be selected to have a strength that is substantially equal to the desired strength for the bond between first structure 400 and second structure 402 and the bond between second structure 402 and third structure 405.

In the depicted example, tension wave 424 and tension wave 430 travel in desired direction 434 and desired direction 436, respectively. These two tension waves may combine at location 446 to form stress zone 442. Different transducer structures with different shapes may be selected for recombining at different depths in these illustrative examples. For example, location 446 may be selected based on a configuration of at least one of reflecting surface 408, reflecting surface 410, and coupling surface 412. In other words, the dimensions of transducer structure 300 may be selected to provide a desired distance within a test object at which tension waves combine with each other.

Figure 5:
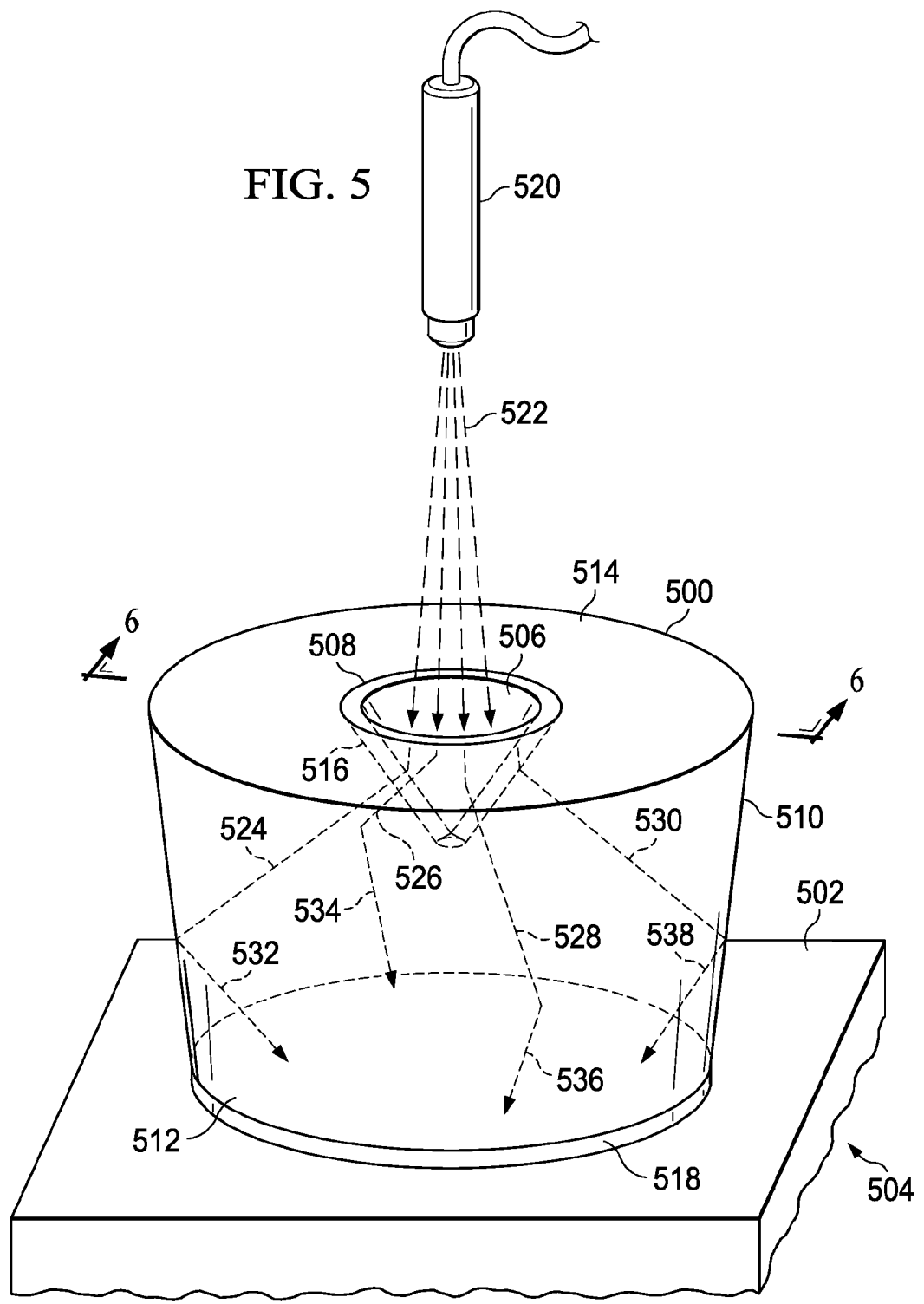
FIG. 5 is an illustration of another configuration for a transducer structure in accordance with an illustrative embodiment.

Turning now to FIG. 5, an illustration of another configuration for a transducer structure is depicted in accordance with an illustrative embodiment. In this illustrative example, transducer structure 500 is located on surface 502 of test object 504.

Transducer structure 500 has a shape of a frustum. As depicted, transducer structure 500 has channel 506 that extends into transducer structure 500. In this illustrative example, channel 506 takes the form of a conical depression. As depicted, transducer structure 500 has absorber surface 508, reflecting surface 510, coupling surface 512, and clamping surface 514.

In these illustrative examples, absorber surface 508 forms the walls of channel 506. Channel 506 has the shape of a cone with the base being located at absorber surface 508. The cone shape of channel 506 reduces in size to form the tip of the cone inside of transducer structure 500.

Absorber 516 is coupled to absorber surface 508. Acoustic matching layer 518 is located between transducer structure 500 and test object 504. In particular, acoustic matching layer 518 is coupled to coupling surface 512 and surface 502 of test object 504. In some cases, a bonding agent may bond acoustic matching layer 518 to test object 504. In still other illustrative examples, acoustic matching layer 518 may also function as a bonding agent.

In these illustrative examples, laser unit 520 generates beam of coherent light 522. Beam of coherent light 522 is directed toward absorber surface 508. In particular, beam of coherent light 522 may be absorbed by absorber 516. When absorber 516 absorbs beam of coherent light 522, the energy in the coherent light causes compression waves to be generated.

These compression waves may travel in different directions inside of transducer structure 500. These compression waves travel toward reflecting surface 510. These directions include, for example, directions 524, 526, 528, and 530 to reflect off of reflecting surface 510. In these illustrative examples, directions 524, 526, 528, and 530 are shown as dotted lines extending through transducer structure 500.

When the compression waves reflect off of reflecting surface 510, the compression waves become tension waves that may travel in directions, such as directions 532, 534, 536, and 538. These tension waves travel through acoustic matching layer 518 into test object 504.

As can be seen, reflecting surface 510 is configured to cause the tension waves to travel in a desired direction into test object 504. In these illustrative examples, the tension waves may be directed at one or more points in test object 504. Further, absorber surface 508 also may have a configuration to cause the compression waves to travel in a desired direction toward reflecting surface 510.

Figure 6:
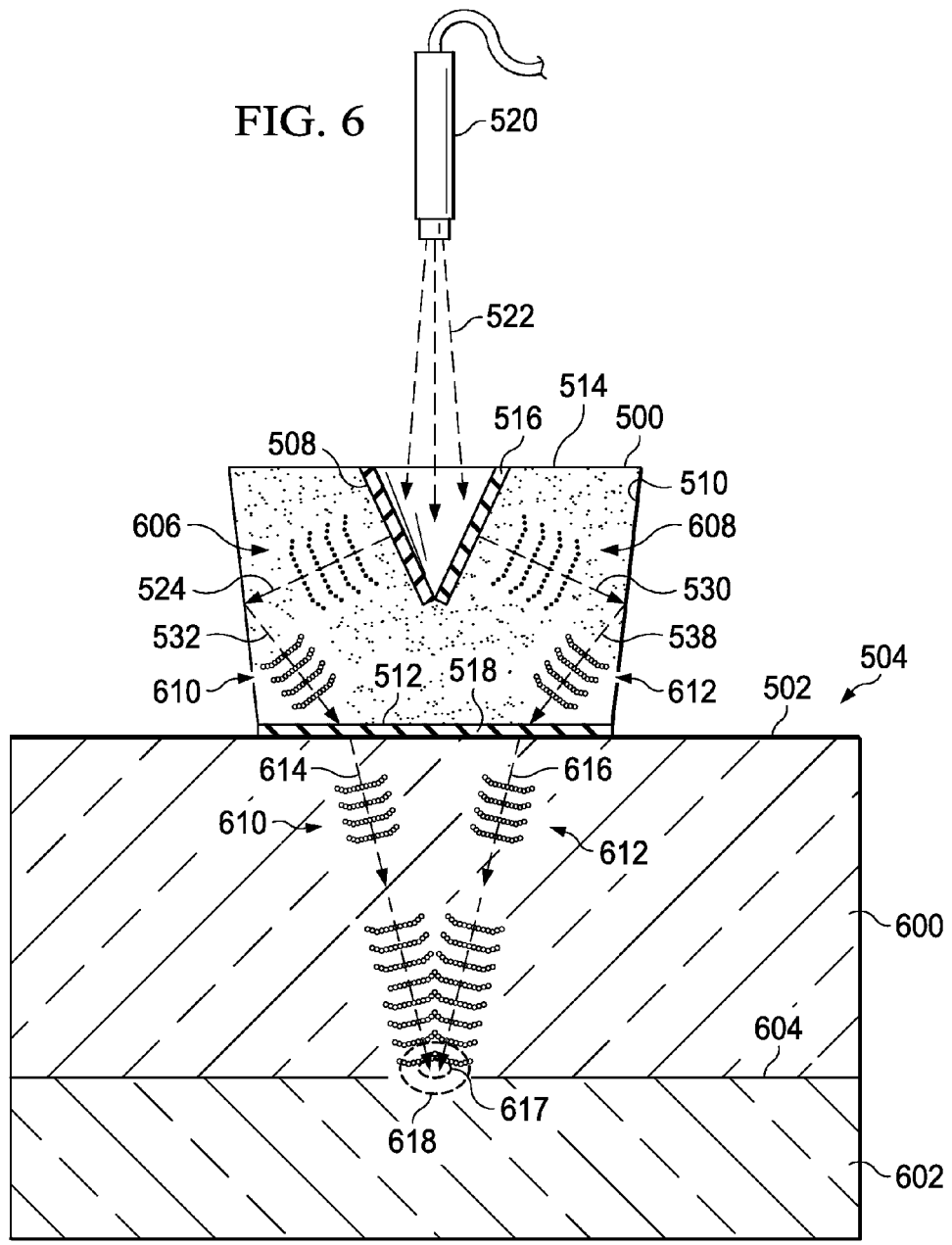
FIG. 6 is an illustration of a cross-sectional view of a transducer system on a test object in accordance with an illustrative embodiment.

Turning now to FIG. 6, an illustration of a cross-sectional view of a transducer system on a test object is depicted in accordance with an illustrative embodiment. In this illustrative example, a cross-sectional view of transducer structure 500 on test object 504 is shown taken along lines 6-6 in FIG. 5.

In this illustrative example, test object 504 is comprised of first structure 600 and second structure 602. These structures are bonded to each other at an interface that forms bond line 604.

As can be seen in this example, beam of coherent light 522 is absorbed by absorber 516. The absorption of coherent light from beam of coherent light 522 generates compression waves, such as compression wave 606 and compression wave 608, that travel in direction 524 and direction 530, respectively, toward reflecting surface 510.

The reflection of these compression waves results in tension wave 610 and tension wave 612 that travel in direction 532 and direction 538, respectively. These tension waves travel through acoustic matching layer 518 into test object 504 in desired direction 614 and desired direction 616 as depicted. In these illustrative examples, desired direction 614 and desired direction 616 may be selected based on the configuration of at least one of absorber surface 508 and reflecting surface 510 for transducer structure 500.

Tension wave 610 and tension wave 612 may travel through test object 504 and may combine at location 617. Location 617 may be a single point or a plane within test object 504. Tension wave 610 and tension wave 612 may generate stress zone 618 at bond line 604. The forces generated by tension wave 610, tension wave 612, and other tension waves tests the strength of a bond between first structure 600 and second structure 602 in test object 504 in these illustrative examples.

If the strength of the bond between first structure 600 and second structure 602 is able to withstand the force generated by the tension waves, inconsistencies do not occur along bond line 604. As a result, the strength of the tension waves may be generated to have a strength that determines whether the bond between first structure 600 and second structure 602 has a desired strength.

Figure 7:
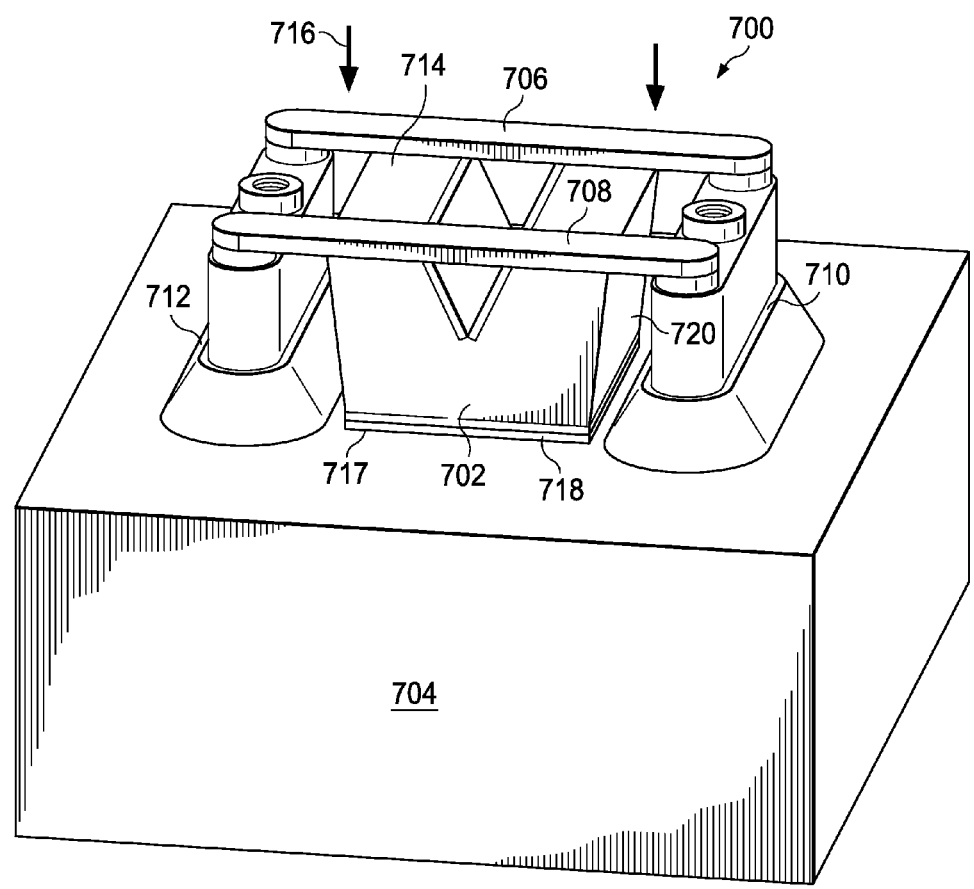
FIG. 7 is an illustration of a coupling system in accordance with an illustrative embodiment.

Turning now to FIG. 7, an illustration of a coupling system is depicted in accordance with an illustrative embodiment. In this illustrative example, coupling system 700 is an example of one type of coupling system that may be used to couple transducer structure 702 to test object 704.

In this illustrative example, coupling system 700 comprises elongate structure 706, elongate structure 708, vacuum unit 710, and vacuum unit 712. Elongate structure 706 and elongate structure 708 may be placed on coupling surface 714 of transducer structure 702. Elongate structure 706 and elongate structure 708 also are connected to vacuum unit 710 and vacuum unit 712. A vacuum may be applied using vacuum unit 710 and vacuum unit 712 to generate force 716 to couple transducer structure 702 to test object 704.

In this illustrative example, coupling system 700 also may include bonding agent 717. Bonding agent 717 may be used to generate a temporary bond between transducer structure 702 and test object 704. In these illustrative examples, bonding agent 717 may be, for example, without limitation, an adhesive, a gel, or some other suitable material. Bonding agent 717 also may serve as an acoustic matching layer, depending on the particular implementation. Alternatively, bonding agent 717 may bond acoustic matching layer 718 to transducer structure 702 and to test object 704.

In these illustrative examples, the tension waves are configured to cause the desired level of stress within test object 704 and not at the bond formed using bonding agent 717. The tension waves may be directed to recombine spatially, in these illustrative examples, to cause the desired level of stress. The recombination may be accomplished by the shape and orientation of reflecting surfaces 720. The shape and orientation of reflecting surfaces 720 may be selected to cause the tension waves to converge and meet below the surface of test object 704. At bonding agent 717, the intensity of the passing tension waves is thus reduced to a level such that bonding agent 717 remains intact.

The illustration of test environment 100, the different components for inspection system 102, transducer structures, test objects, and the coupling system in FIGS. 1-7 are not meant to imply physical or architectural limitations to the manner in which different illustrative embodiments may be implemented. The different embodiments illustrated in these figures are only meant as illustrative examples of how some illustrative embodiments may be implemented. Other illustrative embodiments may include other components in addition to or in place of the ones illustrated.

For example, in some illustrative embodiments, transducer system 132 may be placed in other locations other than on transducer structure 124. For example, transducer system 132 may be placed on test object 104. In still other illustrative examples, transducer system 132 may be omitted. In other illustrative examples, absorber 126 may not be included. In still other illustrative examples, one or more additional transducer structures in addition to transducer structure 124 may be present in test environment 100.

As another example, other shapes for transducer structures may be used in addition to those illustrated in FIGS. 1-7. In yet another illustrative example, the transducer structure may have a shape of a pentagonal frustum, a square frustum, or some other shape. In still other illustrative examples, one or more additional channels may be present in addition to the channel illustrated in the different transducer structures. Each of these additional channels may include absorbing surfaces with absorbers that receive a beam of coherent light to generate compression waves.

Further, other sources of energy may be used in addition to or in place of a beam of coherent light from a laser unit. For example, the source of energy may be projectile impacts, electromagnetic actuators, nail guns, piezo-actuators, pneumatic impact hammers, and other energetic processes that may be used to transfer energy into the surface of the transducer such that tension waves are produced and directed into the test object.

Although the illustrative examples are directed toward using tension waves to test bonds between structures in test objects, the tension waves may be used to test other parts of the test objects. For example, the tension waves may be used to test the strength of the structures themselves in addition to or in place of the bonds between the structures in the test objects.

Although the stress zones are shown with a particular shape or size, the stress zones may have other configurations or sizes. Further, the stress zones are three-dimensional volumes even though these stress zones are illustrated in two dimensions.

Figure 8:
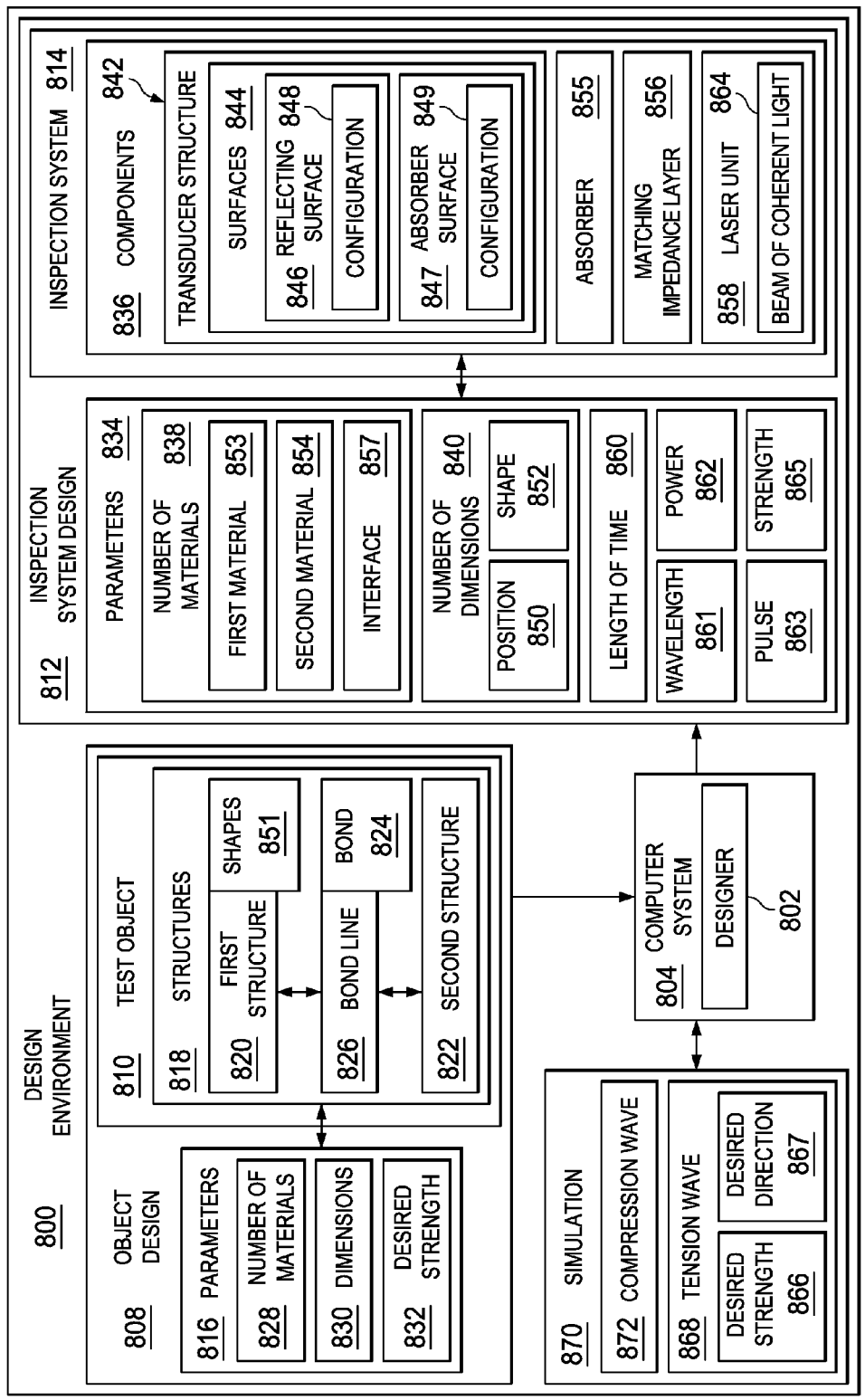
FIG. 8 is an illustration of a block diagram of a design environment in accordance with an illustrative embodiment.

Turning now to FIG. 8, an illustration of a block diagram of a design environment is depicted in accordance with an illustrative embodiment. Design environment 800 may be used to design various components in test environment 100 in FIG. 1. In addition, design environment 800 may be used to design different types of transducer structures, such as those illustrated in FIGS. 2-6, as well as coupling systems, such as those depicted in FIG. 1 and FIG. 7.

In these illustrative examples, design environment 800 includes designer 802. Designer 802 is hardware, software, or a combination of the two.

In this illustrative example, designer 802 may be implemented in computer system 804. Computer system 804 is one or more computers. When more than one computer is present in computer system 804, those computers may be in communication with each other through a communications media. The communications media may be a network, wireless communications links, or some other communications media.

In this illustrative example, designer 802 may use object design 808 for test object 810 as an input to generate or modify inspection system design 812 for inspection system 814.

In these illustrative examples, object design 808 for test object 810 may include parameters 816 for test object 810. Parameters 816 may be parameters for structures 818 that are bonded to each other in test object 810.

For example, structures 818 include first structure 820 and second structure 822 bonded to each other by bond 824. The interface at which first structure 820 is bonded to second structure 822 is bond line 826. In these illustrative examples, parameters 816 may include number of materials 828 and dimensions 830 for structures 818, as well as for bond 824. Additionally, parameters 816 also may include desired strength 832 for bond 824.

With object design 808, designer 802 may generate and/or modify parameters 834 for inspection system 814 in inspection system design 812. These parameters may be selected for at least one of the components in components 836 of inspection system 814.

As depicted, number of materials 838 and number of dimensions 840 may be selected for transducer structure 842. Number of dimensions 840 may include, for example, the configuration for surfaces 844 for transducer structure 842. These surfaces may include reflecting surface 846 and absorber surface 847 in transducer structure 842.

Number of dimensions 840 may be for configuration 848 of reflecting surface 846 and configuration 849 of absorber surface 847. For example, number of dimensions 840 may describe position 850, shape 852, and other features for configuration 848, configuration 849, or both. Shape 852 and position 850 are selected such that tension waves generated using transducer structure 842 travel through test object 810 in a desired direction.

In these illustrative examples, shape 852 may be a planar shape, a concave shape, a convex shape, a random shape, or some other suitable shape, depending on the desired direction for tension waves traveling in test object 810. The design of shape 852 to have a desired direction for the tension waves also may take into account dimensions 830 defining shapes 851 for structures 818 in test object 810. For example, if shapes 851 include irregular shapes, these shapes may be taken into account in selecting number of dimensions 840 for transducer structure 842.

In another illustrative example, number of materials 838 for transducer structure 842 may include first material 853 and second material 854. These materials may be configured to form interface 857. As depicted, interface 857 may be used in transducer structure 842 in place of reflecting surface 846.

In these illustrative examples, the selection of first material 853 and second material 854 may be such that interface 857 between these two materials generates a tension wave. For example, first material 853 may be selected as the portion of transducer structure 842 having absorber surface 847. In other words, first material 853 is the material in which a compression wave is generated.

In the illustrative examples, first material 853 is selected to have a higher acoustic impedance as compared to second material 854. For example, first material 853 may be titanium, while second material 854 may be selected as aluminum, copper, or some other suitable material. In one illustrative example, first material 853 may be a solid, while second material 854 may be a fluid. With this example, transducer structure 842 may be immersed in a fluid, such as a liquid.

As yet another illustrative example, designer 802 may select parameters 834 for absorber 855 in matching impedance layer 856 in inspection system 814. For example, number of materials 838 may specify materials for these components in inspection system 814. Further, number of dimensions 840 also may specify dimensions for absorber 855 and matching impedance layer 856.

As another illustrative example, parameters 834 may include parameters for laser unit 858. In particular, parameters 834 may include length of time 860, wavelength 861, and power 862 for beam of coherent light 864 generated by laser unit 858. Pulse 863 may identify a duration and wavelength of beam of coherent light 864. Strength 865 may identify a strength or energy for beam of coherent light 864. In this manner, desired strength 866 for tension wave 868 may be selected in these illustrative examples.

With object design 808 and inspection system design 812, designer 802 may perform simulation 870. Simulation 870 may be used to simulate the generation of compression wave 872 inside of transducer structure 842. Compression wave 872 reflects off of reflecting surface 846 in transducer structure 842 to travel in desired direction 867 as tension wave 868 travels through test object 810. With this simulation, a determination can be made as to whether the strength for tension wave 868 is desired strength 866 for testing bond 824 between first structure 820 and second structure 822.

In other words, simulation 870 may be used to select strength 865 for beam of coherent light 864 to generate tension wave 868 with desired strength 866 to test bond 824. In these illustrative examples, designer 802 may select parameters 834 automatically, through user input, or both, depending on the particular implementation.

Figure 9:
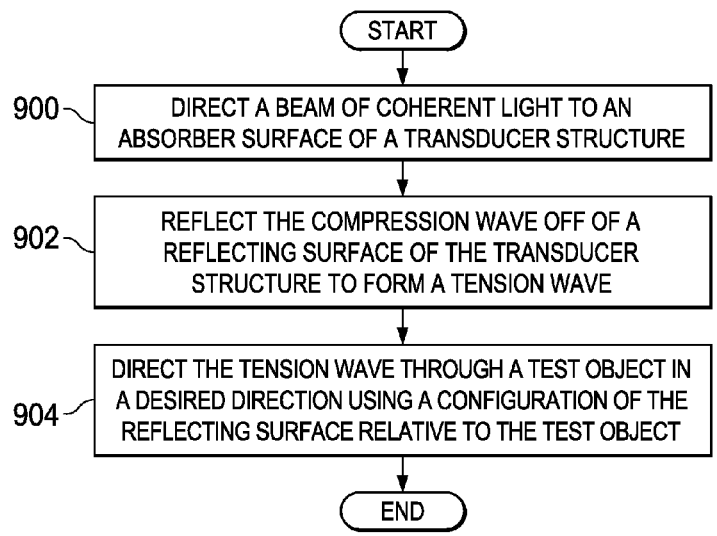
FIG. 9 is an illustration of a flowchart of a process for generating a tension wave in accordance with an illustrative embodiment.

With reference now to FIG. 9, an illustration of a flowchart of a process for generating a tension wave is depicted in accordance with an illustrative embodiment. The process illustrated in FIG. 9 may be implemented in test environment 100 in FIG. 1. This test environment may be generated using design environment 800 in FIG. 8.

The process begins by directing a beam of coherent light to an absorber surface of a transducer structure (operation 900). The beam of coherent light is configured to generate a compression wave within the transducer structure. The compression wave is reflected off of a reflecting surface of the transducer structure to form a tension wave (operation 902).

The tension wave is directed through a test object in a desired direction using a configuration of the reflecting surface relative to the test object (operation 904), with the process terminating thereafter. The directing of the tension wave also may be accomplished based on a configuration of the absorber surface on the transducer structure.

Figure 10:
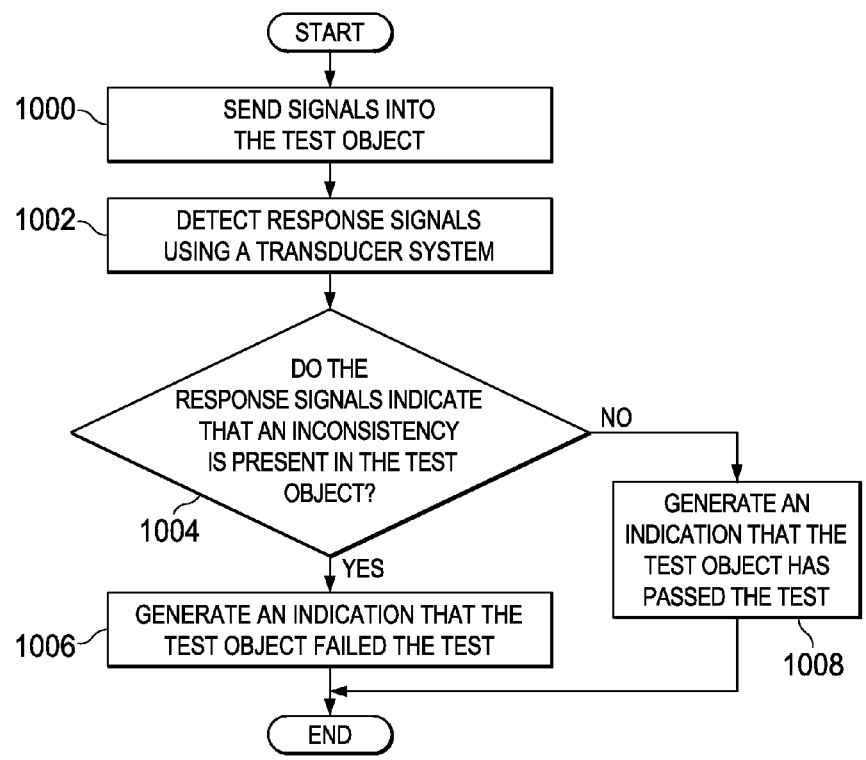
FIG. 10 is an illustration of a flowchart of a process for testing a test object in accordance with an illustrative embodiment.

With reference now to FIG. 10, an illustration of a flowchart of a process for testing a test object is depicted in accordance with an illustrative embodiment. This process may be implemented after a tension wave has been sent through a test object. The process may be implemented using design environment 800 in FIG. 8.

The process begins by sending signals into the test object (operation 1000). The process then detects response signals using a transducer system (operation 1002). In these illustrative examples, the transducer system may be a piezoelectric transducer system.

The signals may be sent into the test object in a number of different ways. For example, the process may include sending another tension wave through the test object or generating signals using the transducer system. If the response signals are generated using another tension wave generated by the transducer structure, the second tension wave is selected to have a strength that avoids causing inconsistencies in the bond between the first structure and the second structure of the test object.

A determination is made as to whether the response signals indicate that an inconsistency is present in the test object (operation 1004). If an inconsistency is present, an indication is generated that the test object failed the test (operation 1006), with the process terminating thereafter.

With reference again to operation 1004, if an inconsistency is not present, the process generates an indication that the test object has passed the test (operation 1008), with the process terminating thereafter. In this case, the bond in the test object has held up to the forces generated on the bond by the tension waves. As a result, this test object may be certified as withstanding the force selected for testing.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent a module, segment, function, and/or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram.

Figure 11:
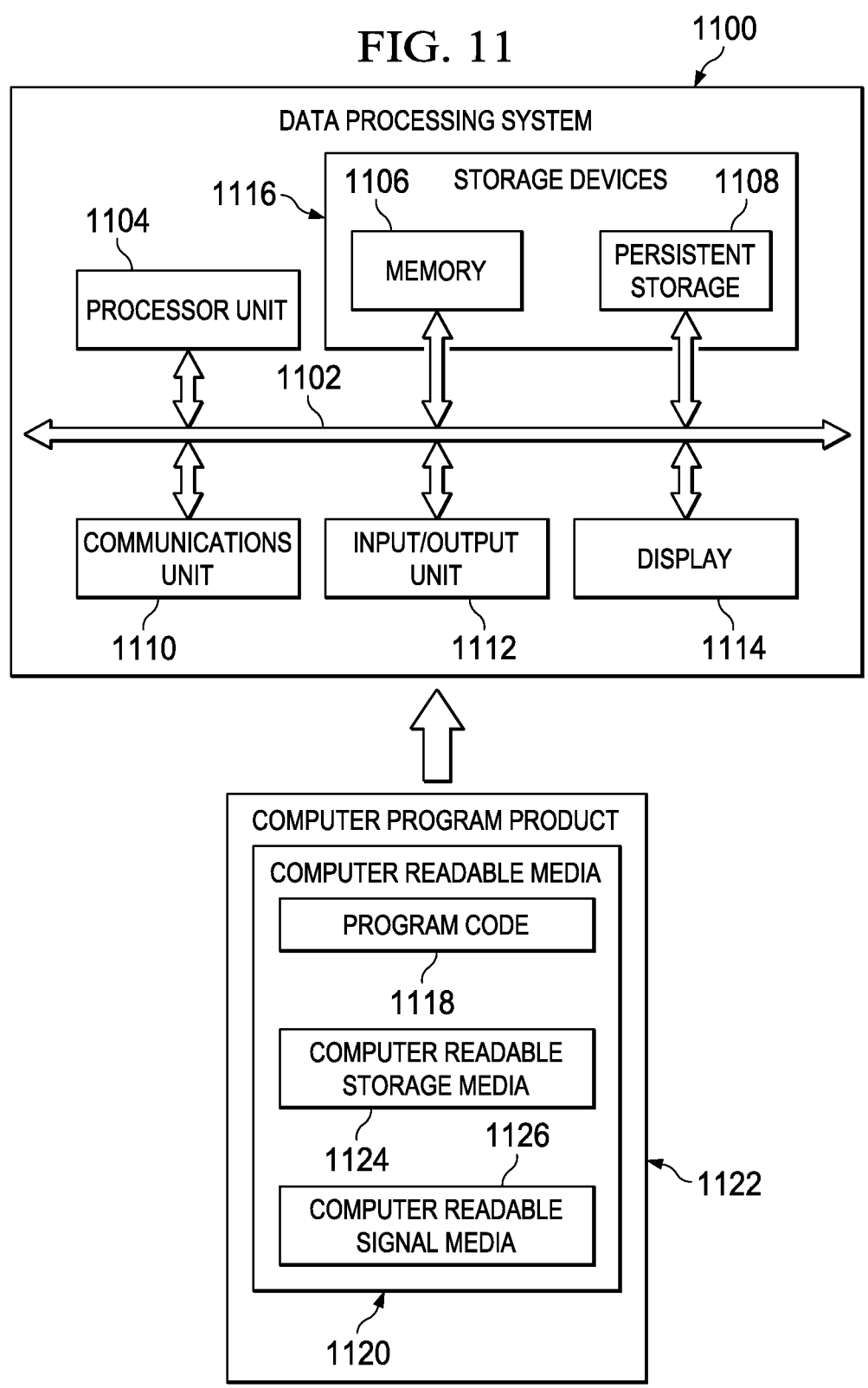
FIG. 11 is an illustration of a data processing system in accordance with an illustrative embodiment.

Turning now to FIG. 11, an illustration of a data processing system is depicted in accordance with an illustrative embodiment. Data processing system 1100 may be used to implement computer 118 in FIG. 1 and one or more computers in computer system 804 in FIG. 8. In this illustrative example, data processing system 1100 includes communications framework 1102, which provides communications between processor unit 1104, memory 1106, persistent storage 1108, communications unit 1110, input/output (I/O) unit 1112, and display 1114. In this example, communication framework 1102 may take the form of a bus system.

Processor unit 1104 serves to execute instructions for software that may be loaded into memory 1106. Processor unit 1104 may be a number of processors, a multi-processor core, or some other type of processor, depending on the particular implementation.

Memory 1106 and persistent storage 1108 are examples of storage devices 1116. A storage device is any piece of hardware that is capable of storing information, such as, for example, without limitation, data, program code in functional form, and/or other suitable information either on a temporary basis and/or a permanent basis. Storage devices 1116 may also be referred to as computer readable storage devices in these illustrative examples. Memory 1106, in these examples, may be, for example, a random access memory or any other suitable volatile or non-volatile storage device. Persistent storage 1108 may take various forms, depending on the particular implementation.

For example, persistent storage 1108 may contain one or more components or devices. For example, persistent storage 1108 may be a hard drive, a flash memory, a rewritable optical disk, a rewritable magnetic tape, or some combination of the above.

Communications unit 1110, in these illustrative examples, provides for communications with other data processing systems or devices. In these illustrative examples, communications unit 1110 is a network interface card.

Input/output unit 1112 allows for input and output of data with other devices that may be connected to data processing system 1100. For example, input/output unit 1112 may provide a connection for user input through a keyboard, a mouse, and/or some other suitable input device. Display 1114 provides a mechanism to display information to a user.

Instructions for the operating system, applications, and/or programs may be located in storage devices 1116, which are in communication with processor unit 1104 through communications framework 1102. The processes of the different embodiments may be performed by processor unit 1104 using computer-implemented instructions, which may be located in a memory, such as memory 1106.

These instructions are referred to as program code, computer usable program code, or computer readable program code that may be read and executed by a processor in processor unit 1104. The program code in the different embodiments may be embodied on different physical or computer readable storage media, such as memory 1106 or persistent storage 1108.

Program code 1118 is located in a functional form on computer readable media 1120 that is selectively removable and may be loaded onto or transferred to data processing system 1100 for execution by processor unit 1104. Program code 1118 and computer readable media 1120 form computer program product 1122 in these illustrative examples. In one example, computer readable media 1120 may be computer readable storage media 1124 or computer readable signal media 1126.

In these illustrative examples, computer readable storage media 1124 is a physical or tangible storage device used to store program code 1118 rather than a medium that propagates or transmits program code 1118.

Alternatively, program code 1118 may be transferred to data processing system 1100 using computer readable signal media 1126. Computer readable signal media 1126 may be, for example, a propagated data signal containing program code 1118. For example, computer readable signal media 1126 may be an electromagnetic signal, an optical signal, and/or any other suitable type of signal. These signals may be transmitted over communications links, such as wireless communications links, optical fiber cable, coaxial cable, a wire, and/or any other suitable type of communications link.

The different components illustrated for data processing system 1100 are not meant to provide architectural limitations to the manner in which different embodiments may be implemented. The different illustrative embodiments may be implemented in a data processing system including components in addition to and/or in place of those illustrated for data processing system 1100. Other components shown in FIG. 11 can be varied from the illustrative examples shown. The different embodiments may be implemented using any hardware device or system capable of running program code 1118.

Figure 12:
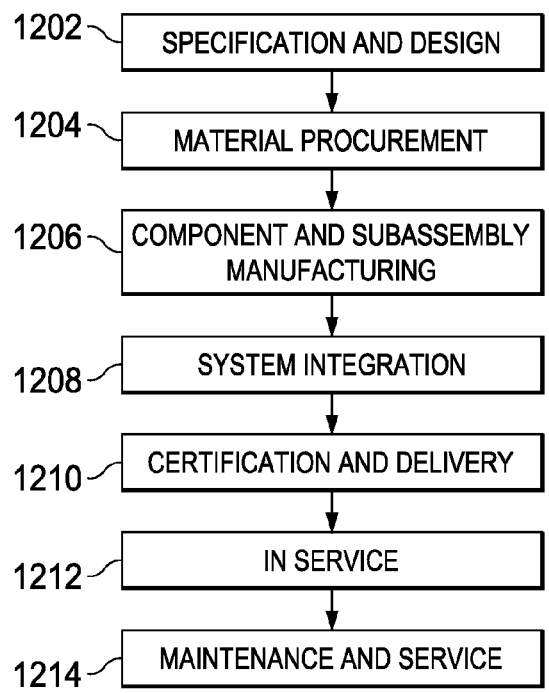
FIG. 12 is an illustration of an aircraft manufacturing and service method in accordance with an illustrative embodiment.
Figure 13:
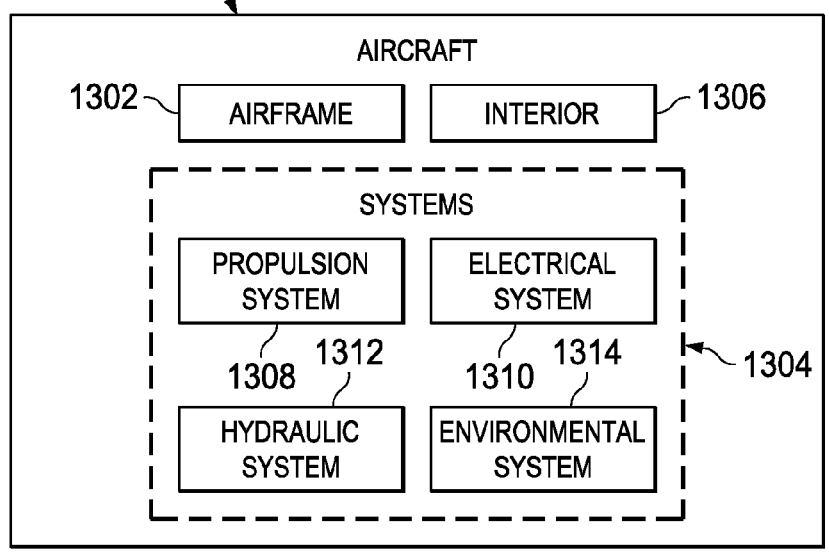
FIG. 13 is an illustration of an aircraft in which an illustrative embodiment may be implemented.

Illustrative embodiments of the disclosure may be described in the context of aircraft manufacturing and service method 1200 as shown in FIG. 12 and aircraft 1300 as shown in FIG. 13. Turning first to FIG. 12, an illustration of an aircraft manufacturing and service method is depicted in accordance with an illustrative embodiment. During pre-production, aircraft manufacturing and service method 1200 may include specification and design 1202 of aircraft 1300 in FIG. 13 and material procurement 1204.

During production, component and subassembly manufacturing 1206 and system integration 1208 of aircraft 1300 takes place. Thereafter, aircraft 1300 may go through certification and delivery 1210 in order to be placed in service 1212. While in service 1212 by a customer, aircraft 1300 is scheduled for routine maintenance and service 1214, which may include modification, reconfiguration, refurbishment, and other maintenance or service.

Each of the processes of aircraft manufacturing and service method 1200 may be performed or carried out by a system integrator, a third party, and/or an operator. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 13, an illustration of an aircraft is depicted in which an illustrative embodiment may be implemented. In this example, aircraft 1300 is produced by aircraft manufacturing and service method 1200 in FIG. 12 and may include airframe 1302 with plurality of systems 1304 and interior 1306. Examples of systems 1304 include one or more of propulsion system 1308, electrical system 1310, hydraulic system 1312, and environmental system 1314. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1200 in FIG. 12. For example, one or more illustrative embodiments may be implemented during component and subassembly manufacturing 1206 to test objects manufactured during this phase. In another illustrative example, one or more illustrative embodiments may be implemented during certification and delivery 1210 to test objects for certification. In still other illustrative examples, one or more illustrative embodiments may be implemented while aircraft 1300 is in service 1212 or during maintenance and service 1214 to test structures in aircraft 1300.

Thus, one or more illustrative embodiments provide a method and apparatus for testing bond strength in composite structures. In the illustrative embodiments, a compression wave may be generated in a transducer structure in which the compression wave travels to a reflecting surface. The reflecting surface is a free surface. In other words, the reflecting surface is open to the air or environment. The reflection of the compression wave generates a tension wave that is directed through the transducer structure into a test object. In these illustrative examples, the test object may be a composite object containing two or more composite structures bonded to each other. The tension wave may test the bond strength between these structures. For example, the bonds may be joints in a structure. The illustrative embodiments may be used to test bonds in structures that have irregular shapes or thicknesses.

Additionally, with one or more illustrative embodiments, a greater control over the generation of tension waves in a test object is present as compared to currently used systems for testing. With a transducer structure, in accordance with an illustrative embodiment, bonds, material properties of structures, and other features may be tested. The tests may be performed for these features at different depths without concern for the location and shape of the back surface of the material under testing. This back surface is the surface on the opposite side of the surface on which the transducer structure is placed.

Further, fewer losses occur in generating a tension wave using an illustrative embodiment. For example, the compression wave travels through the transducer structure. The transducer structure may be selected to have a material that has a lower acoustic impedance as compared to the materials in the test object.

The description of the different illustrative embodiments has been presented for purposes of illustration and description and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for generating a tension wave, the method comprising:
    directing a beam of coherent light to an absorber surface of a transducer structure, wherein a compression wave is generated within the transducer structure;
    reflecting the compression wave on a reflecting surface of the transducer structure to form the tension wave; and
    directing the tension wave through a test object in a desired direction using a configuration of the reflecting surface relative to the test object.

2. The method of claim 1, wherein directing the beam of coherent light to the absorber surface of the transducer structure, wherein the compression wave is generated within the transducer structure comprises:
    directing the beam of coherent light to an absorber connected to the absorber surface of the transducer structure, wherein the absorber is configured to absorb the beam of coherent light and generate the compression wave within the transducer structure.

3. The method of claim 2, wherein the compression wave travels through the transducer structure to the reflecting surface and forms the tension wave that travels in the desired direction through the transducer structure through a coupling surface of the transducer structure coupled to the test object.

4. The method of claim 1, wherein the test object is comprised of a first structure and a second structure bonded to each other at a bond line.

5. The method of claim 4, wherein the desired direction for the tension wave is through the bond line.

6. The method of claim 5, wherein the tension wave has a strength configured to test a strength of the bond line and further comprising:
    determining whether an inconsistency is present in the bond line after the tension wave passes through the bond line.

7. The method of claim 6, wherein the beam of coherent light is a first beam of coherent light, the compression wave is a first compression wave, the tension wave is a first tension wave having a first strength and determining whether the inconsistency is present in the bond line after the tension wave passes through the bond line comprises:
    sending a second beam of coherent light to the absorber surface of the transducer structure, wherein a second compression wave is generated within the transducer structure;
    reflecting the second compression wave on the reflecting surface of the transducer structure to form a second tension wave;
    directing the second tension wave through the test object in the desired direction using the configuration of the reflecting surface relative to the test object;
    sending the second tension wave in the desired direction through the bond line after the first tension wave passes through the bond line, wherein the second tension wave has a second strength that is selected to avoid causing inconsistencies in the bond line;
    detecting a response signal generated by the second tension wave; and
    determining whether the inconsistency is present using the response signal.

8. The method of claim 7, wherein the response signal is detected using a piezoelectric transducer.

9. The method of claim 1, wherein the transducer structure is a prism.

10. The method of claim 1, wherein the transducer structure includes a channel extending into the transducer structure and the channel has a shape of a cone, wherein walls of the channel form the reflecting surface.

11. The method of claim 1, wherein the transducer structure includes a channel across a side of the transducer structure and the channel has a cross section with a v-shape, wherein walls of the channel form the reflecting surface.

12. A method for generating a tension wave, the method comprising:
    directing a laser beam to an absorber connected to an absorber surface of a transducer structure, wherein the absorber is configured to absorb energy in the laser beam and generate a compression wave within the transducer structure;
    reflecting the compression wave on a reflecting surface of the transducer structure to form the tension wave; and
    directing the tension wave through a test object in a desired direction, wherein the reflecting surface has a configuration relative to the test object that causes the tension wave to move in the desired direction.

13. The method of claim 12 further comprising:
    applying a force on the transducer structure, wherein the force is configured to maintain a coupling between the transducer structure and the test object such that a transfer of energy in the tension wave from the transducer structure into the test object increases.

14. An apparatus comprising:
    a transducer structure;
    an absorber surface on the transducer structure configured to receive energy configured to cause a compression wave;
    a reflecting surface on the transducer structure configured to reflect the compression wave traveling from the absorber surface to generate a tension wave in a desired direction using a configuration of the reflecting surface in which the compression wave is generated by an absorber coupled to the absorber surface and absorbs the energy from a beam of coherent light; and
    a coupling surface on the transducer structure configured to be coupled to a test object, wherein the tension wave travels through the test object in the desired direction.

15. The apparatus of claim 14 further comprising:
a laser unit configured to generate the beam of coherent light.

16. The apparatus of claim 14 further comprising:
an acoustic matching layer configured to be located between the transducer structure and the test object and to increase a transfer of energy in the tension wave from the transducer structure into the test object.

17. The apparatus of claim 14 further comprising:
an absorber configured to be connected to the absorber surface, wherein the absorber is comprised of a material selected from at least one of carbon black, black chrome plating, pyrolytic carbon, flat black paint, and vinyl tape.

18. The apparatus of claim 14 further comprising:
a transducer system configured to detect an inconsistency in the test object.

19. The apparatus of claim 14 further comprising:
a coupling system configured to couple the transducer structure to the test object such that a transfer of energy in the tension wave from the transducer structure into the test object increases.

20. The apparatus of claim 14, wherein the transducer structure is comprised of a material selected from at least one of a metal, a metal alloy, steel, aluminum, and titanium.

* * * * *